United States Patent [19]

Crowley et al.

[11] Patent Number: 5,750,778
[45] Date of Patent: May 12, 1998

[54] FUNGICIDE INTERMEDIATES

[75] Inventors: Patrick Jelf Crowley, Crowthorne; Kevin Robert Lawson, High Wycombe; Douglas John Smith, Bracknell; Donn Warwick Moseley, Reading, all of England

[73] Assignee: Zeneca Limited, London, England

[21] Appl. No.: 105,650

[22] Filed: Aug. 10, 1993

Related U.S. Application Data

[63] Continuation of Ser. No. 736,347, Jul. 26, 1991, abandoned.

[30] Foreign Application Priority Data

Jul. 27, 1990 [GB] United Kingdom ............... 9016577
Apr. 17, 1991 [GB] United Kingdom ............... 9108216

[51] Int. Cl.$^6$ .............................................. C07C 53/21
[52] U.S. Cl. ................................. 562/605; 562/840
[58] Field of Search ........................... 562/605, 840; 560/111, 219, 227

[56] References Cited

U.S. PATENT DOCUMENTS

| | | | |
|---|---|---|---|
| 4,030,994 | 6/1977 | Kollonitsch | 562/405 |
| 4,036,871 | 7/1977 | Holland et al. | 260/41.8 D |
| 4,055,574 | 10/1977 | Ackrell et al. | 514/906 |
| 4,187,381 | 2/1980 | Holland et al. | 560/121 |
| 4,206,137 | 6/1980 | Condon et al. | 562/504 |
| 4,588,837 | 5/1986 | Baasner et al. | 562/605 |
| 4,663,320 | 5/1987 | Jones et al. | 514/233.2 |
| 4,663,336 | 5/1987 | Nakame et al. | 514/381 |
| 4,663,337 | 5/1987 | Das et al. | 514/382 |
| 4,665,091 | 5/1987 | Hoffman | 514/450 |
| 4,999,381 | 3/1991 | Crowley et al. | 514/618 |
| 5,126,482 | 6/1992 | Nakai et al. | 554/150 |

FOREIGN PATENT DOCUMENTS

| | | | |
|---|---|---|---|
| 381330 | 8/1990 | European Pat. Off. | |
| 0411153 | 2/1991 | European Pat. Off. | |
| 2350119 | 4/1975 | Germany | 562/861 |
| 3-141241 | 6/1991 | Japan | |

OTHER PUBLICATIONS

Arora, Parkash C., et al., "Electrolysis of α-Chloro-and α-Fluoro-carboxylic Acids", Can. J. Chem., 1971, 49(16), 2681–7.
Chemical Abstracts (1968) vol. 68, 77920m.
Bulletin de la Societe Chimique de France, (1967) No. 10, pp. 3904–3909.
Chemical Abstracts (1990) vol. 112, 118263x.
Chemical Abstracts (1982) vol. 97, 144272r.
Pattison et al., Can J. Chem, 43(6), pp. 1700–1713 (1965).
CA 75(18) : 115271e, 1971.
CA 94(17) : 138858h, 1980.

Primary Examiner—Alan L. Rotman
Assistant Examiner—Jean F. Vollano
Attorney, Agent, or Firm—Marian T. Thomson

[57] ABSTRACT

Certain fluoroalkanoic acids and derivatives, including 2-fluoroisobutyric acid and 2-fluoroisobutyryl chloride, useful as intermediates for fungicides, and methods of preparing them.

7 Claims, No Drawings

FUNGICIDE INTERMEDIATES

This application is a continuation of application Ser. No. 07/736,347 filed on Jul. 26, 1991 now abandoned.

This invention relates to fluoroalkanoic acids and derivatives thereof, which are useful intermediates in the preparation of fungicides, and to methods of preparing them.

Certain fluoroalkanoic acids and derivatives are described in, for example, Chemical Abstracts (CA 77(9):61234r, CA 83(1):10242h, CA 107(25):236013k, and CA 112(23):216382e) and in *J. Org. Chem* 1986,51 (7), 1003–6, *Can. J. Chem* 1971, 49(16), 2681–7, and *Bull. Soc. Chim. Fr* 1967(10), 3904–9. In U.S. Pat. No. 4,030,994 there is described the fluorination of isobutyric acid which is reported as giving a mixture of some isobutyric acid, 2-fluoroisobutyric acid and 3-fluoroisobutyric acid.

According to the present invention there are provided fluoroalkanoic acids and derivatives thereof of the formula (I), wherein R is OH, Cl, $C_{1-8}$ alkoxy or optionally substituted benzyloxy; $R^1$ is methyl, ethyl, $CH_2F$ or $CF_3$; and, when $R^1$ is methyl, ethyl or $CH_2F$, $R^2$ is ethyl, n- or iso-propyl, allyl, optionally substituted benzyl, propargyl or $CHFR^3$ wherein $R^3$ is H, methyl or ethyl, and, when $R^1$ is $CF_3$, $R^2$ is vinyl, 1-propenyl or the group $C(R^4)(R^5)R^6$ wherein $R^4$ is H, methyl or ethyl, $R^5$ is H, F, Br, methyl or ethyl and $R^6$ is H or F, or $R^1$ and $R^2$ are both methyl and R is Cl, $C_{3-8}$ alkoxy or OH, the compound in which R is OH being in substantially pure form; provided that when $R^1$ is methyl and $R^2$ is ethyl, allyl or benzyl, R is not ethoxy, that when $R^1$ is methyl and $R^2$ is $CH_2F$, R is not methoxy, that when $R^1$ and $R^2$ are both ethyl, R is not OH or ethoxy and that when $R^1$ is $CF_3$ and $R^2$ is methyl, R is not methoxy.

$C_{1-8}$ Alkoxy and $C_{3-8}$ alkoxy mean alkoxy groups containing from 1 to 8 carbon atoms and from 3 to 8 carbon atoms, respectively, which can be in the form of straight or branched chains. Examples are methoxy, ethoxy, n-propyloxy, n-butoxy, tert-butoxy, n-hexyloxy and n-octyloxy.

Optionally substituted benzyl and the optionally substituted benzyl moiety in "benzyloxy" include benzyl and benzyl in which the phenyl ring is substituted with one or more of, for example, halogen, $C_{1-4}$ alkyl and $C_{1-4}$ alkoxy.

The compounds of the invention are useful intermediates in the preparation of fungicidal compounds of the type described in EP-A-0381330.

In one aspect of the invention there are provided compounds of the formula (I) wherein R is OH or Cl; $R^1$ is methyl, $CF_3$ or $CH_2F$, and, when $R^1$ is methyl or $CH_2F$, $R^2$ is ethyl, n or iso-propyl, allyl, propargyl or $CHFR^3$ wherein $R^3$ is H, methyl or ethyl, and, when $R^1$ is $CF_3$, $R^2$ is the group $C(R^4)(R^5)R^6$ wherein $R^4$ is H, methyl or ethyl, $R^5$ is H, F, Br, methyl or ethyl and $R^6$ is H or F.

In another aspect of the invention there are provided compounds of the formula (I) wherein R is OH; $R^1$ is methyl or $CF_3$; and, when $R^1$ is methyl, $R^2$ is ethyl, n-propyl or $CH_2F$, and, when $R^1$ is $CF_3$, $R^2$ is methyl, $CH_2F$ or $CHFCH_3$.

In yet another aspect of the invention, there are provided 2-fluoroisobutyric acid in substantially pure form and its acid chloride derivative, 2-fluoroisobutyryl chloride. These compounds have the respective formulae (II) and (III), and are particularly useful for the preparation of fungicides described in UK Applications Nos. 9016578.8, 9016579.6, 9016580.4 and 9016581.2 and applications claiming priority therefrom.

The invention also includes 2-fluoroisobutyric acid in the absence of isobutyric acid and 2-fluoroisobutyric acid in the absence of 3-fluoroisobutyric acid.

The invention is illustrated by the compounds listed in the following table. The compounds have the formula (I), in which R, $R^1$ and $R^2$ have the values given in the table.

| R | $R^1$ | $R^2$ | R | $R^1$ | $R^2$ |
|---|---|---|---|---|---|
| OH | $CH_3$ | $CH_3$ | Cl | $CH_3$ | $CH_3$ |
| OH | $CH_3$ | $C_2H_5$ | OH | $CH_3$ | $n$-$C_3H_7$ |
| OH | $CH_3$ | $CH_2CH=CH_2$ | OH | $CH_3$ | $CH_2C\equiv CH$ |
| $OCH_3$ | $C_2H_5$ | $C_2H_5$ | Cl | $C_2H_5$ | $C_2H_5$ |
| OH | $CH_3$ | $CH_2F$ | OH | $CF_3$ | $CH_2F$ |
| $OCH_3$ | $CF_3$ | $CH_2F$ | OH | $CF_3$ | $CHFCH_3$ |
| $OCH_3$ | $CF_3$ | $CHFCH_3$ | OH | $CH_3$ | $CHFCH_3$ |
| OH | $C_2H_5$ | $CHFCH_3$ | OH | $CH_3$ | $CHFC_2H_5$ |
| OH | $CH_2F$ | $CH_2F$ | OH | $CH_3$ | $i$-$C_3H_7$ |
|  |  |  | OH | $CH_3$ | $CH_2C_6H_5$ |

The compounds of the invention may be prepared as described in Routes 1 to 9, which follow. Unless otherwise stated, $R^1$, $R^2$, $R^3$, $R^4$, $R^5$ and $R^6$ have the meanings already given, R' is $C_{1-8}$ alkyl or optionally substituted benzyl, R" is H or $C_{1-8}$ alkyl, $R^7$ and $R^8$ are $C_{1-4}$ alkyl or joined to form a piperidine, pyrrolidine or morpholine ring, Y is O or $H_2$, X is OP where P is a protecting group or OR, and X' is OR' or a dialkylamino group.

Route 1

In Route 1, 2-hydroxyacetic acid esters of formula (IV) are converted to 2-fluoroacetic acid esters of formula (VI) by reaction with one or more equivalents of a dialkylaminosulphur trifluoride of formula (V). The reaction may be carried out in a dry solvent such as methylene chloride, chloroform or fluorotrichloromethane (preferably in methylene chloride), at a temperature of −78° C. to +50° C. The compounds of formula (V) are suitably added to the compounds of formula (IV) at −78° C., warmed to room temperature, and allowed to stand for 5–48 hours. The product of formula (VI) may then be isolated by pouring the reaction mixture onto ice, separating and drying the organic layer, and then carefully evaporating the organic solvent.

Route 2

In Route 2, 2-hydroxyacetic acid esters of formula (IV) are converted to 2-fluoroacetic acid esters of formula (VI), by reaction with sulphur tetrafluoride, with or without a solvent such as arcton 113 or anhydrous hydrogen fluoride (preferably with anhydrous hydrogen fluoride) in an autoclave, at −78° C. to +100° C. (preferably between −40° C. and +30° C.) for 5 to 48 hours (preferably from 10 to 20 hours). The product (VI) may be isolated by cooling to room temperature and venting excess pressure, pouring onto ice and water and extracting with a suitable solvent, for example methylene chloride. The organic solution can then be dried and carefully evaporated to give the 2-fluoroacetic acid ester (VI).

Route 3

In Route 3, a 2-fluoroacetic ester of formula (VII) is reacted with one or more equivalents of a strong base such as a lithium dialkylamide (for example lithium diisopropylamide), in a suitable solvent, such as THF or diethyl ether in an inert atmosphere (for example nitrogen), at −78° C. to +25° C. (preferably at −78° C. to −20° C). The resulting anion may then be treated with one or more equivalents of an alkylating agent (or alkenylating or alkynylating agent), $R^2L$, wherein $R^2$ is as already defined and L is a leaving group, such as iodide, bromide, sulphate or methylsulphonate, and the reaction mixture allowed to warm to room temperature, and then to stand for 1–48 hours. The product (VI), wherein $R^2$ is an alkyl (or alkenyl or alkynyl) group, may be isolated by careful addition of water to the reaction mixture, and extraction with a low boiling organic solvent such as diethyl ether or methylene chloride. After drying, the solvent can be carefully evaporated to yield the product (VI).

Route 4

In Route 4, a 2-fluoroacetic acid (VIII) is reacted with two or more equivalents (preferably three equivalents) of a strong base such as a lithium dialkylamide (for example lithium diisopropylamide) in a suitable solvent such as THF or diethyl ether, in an inert atmosphere (for example nitrogen), at −78° C. to +25° C. (preferably at −78° C. to −50° C.), for ½ to 5 hours. An alkylating agent (or alkenylating or alkynylating agent), $R^2L$, wherein $R^2$ and L are already defined, is then added, and the reaction mixture warmed to room temperature and allowed to stand for 1 to 48 hours. The compound (IX), wherein $R^2$ is an alkyl (or alkenyl or alkynyl) group, may be isolated by adding aqueous mineral acid, for example dilute hydrochloric acid, and extracting with an organic solvent such as methylene chloride or diethyl ether. The organic solution can be dried and evaporated to give the compound (IX).

Route 5

In Route 5, compounds of formula (VI) are converted to a 2-fluoroacetic acid (IX) by hydrolysis with aqueous acid such as hydrochloric acid or sulphuric acid at 0° C. to 120° C. (preferably at 60°–80° C.), for 1 to 48 hours, (preferably for 6–10 hours). The acid (IX) may be isolated by extraction with an organic solvent, such as ethyl acetate or toluene, drying the solvent and evaporating the solvent carefully.

Route 6

In Route 6, the hydrolysis is carried out under basic conditions. For example the ester of formula (VI) may be reacted with an alkali metal hydroxide (such as sodium hydroxide) in a suitable solvent such as aqueous ethanol, or in a two phase system, such as methylene chloride and water containing a phase transfer catalyst (such as cetrimide). The acid (IX) may be isolated by acidifying the solution with aqueous acid (for example dilute hydrochloric acid) and extracting with a suitable solvent such as methylene chloride. The organic solution can be dried and evaporated to give the acid (IX).

Route 7

In Route 7, the acid (IX) is converted to the acid chloride (X) by reaction with reagents such as thionyl chloride, oxalyl chloride, phosphorus trichloride or phosphorus pentachloride (preferably thionyl chloride or oxalyl chloride), either neat, or in a suitable dry solvent such as methylene chloride, chloroform, diethyl ether or toluene at −30° C. to 100° C. (preferably at 0° C. to 40° C). A small quantity of N,N-dimethylformamide may be added to accelarate the reaction. If a solvent is used, the acid chloride (X) can then be used directly as a solution, or can be isolated by careful evaporation of the solvent, and distilled or used directly. If no solvent is used, the volatile components can be carefully evaporated, and the acid chloride distilled, or used directly.

Route 8

In Route 8, an oxirane (XI) is treated with a triethylamine/hydrogen fluoride complex at an elevated temperature, for example, 90° C. to form a mixture of the alcohols (XII) and (XIII). The reaction mixture can be neutralised with sodium bicarbonate and the mixed products extracted with a suitable solvent, such as ether. Diethylaminosulphur trifluoride is added carefully to the mixed products in a solvent such as dichloromethane under an atmosphere of nitrogen at about 0° C. The reaction mixture is drowned in water and the difluoro compound (XIV) extracted with a solvent such as hexane. The difluoro compound (XIV) can be converted to the product (XV) by methods described in the literature. For instance, where Y is $H_2$ and X is OP, the protecting group P which may be, for example, benzoyl, is removed by conventional techniques and the alcohol so formed oxidised to the acid (XV), where R" is H.

Route 9

In Route 9, a compound of formula (XVI) is treated first with di-n-butylboron trifluoromethanesulphonate in ethyl diisopropylamine and then with an aldehyde of formula $R^4CHO$ to give the compound (XVII). The compound (XVII) is converted to the compound (XVIII) by modification of the hydroxyl group and conversion of X' to OR" using methods described in the literature. Typical methods for modification of the hydroxyl group include fluorination (to give a compound (XVIII) where $R^5$ is F and $R^6$ is H); bromination (to give a compound (XVIII) where $R^5$ is Br and $R^6$ is H); reduction of the bromo compound (to give a compound (XVIII) where $R^5$ and $R^6$ are both H); conversion to a leaving group L to give a compound (XVIII) where $R^5$ is L and $R^6$ is H, followed by elimination by treatment with base to give a compound (XIX) where $R^9$ is H or methyl; hydrogenation of compound (XIX) to give a compound (XVIII) where $R^4$ and $R^6$ are H and $R^5$ is methyl or ethyl; oxidation to a keto group and subsequent fluorination (to give a compound (XVIII) where $R^5$ and $R^6$ are both F).

In another aspect the invention includes methods of preparing compound (I) as herein defined.

The invention is illustrated by the following Examples. Where shown, NMR data are selective; no attempt is made to list every absorption in all cases. $^1H$ NMR spectra were recorded using $CDCl_3$ solutions unless otherwise stated. $^1H$ NMR spectra used $(CH_3)_4Si$ as internal standard. $^{19}$ FNMR spectra used $CFCl_3$ as internal standard. The following abbreviations are used throughout:

| NMR = | nuclear magnetic resonance | gc = | gas chromatography | d = | doublet |
|---|---|---|---|---|---|
| THF = | tetrahydrofuran | dd = | double doublet | t = | triplet |
| HF = | hydrogen fluoride | dt = | double triplet | q = | quintet |
| $MgSO_4$ = | magnesium sulphate | m = | multiplet | b = | broad |
| NaOH = | sodium hydroxide | | | | |

EXAMPLE 1

This Example illustrates the preparation of ethyl 2-fluoroisobutyrate by Route 1.

Ethyl 2-hydroxyisobutyrate (12.43 g) was stirred in dry methylene chloride (65 ml) at −70° C. under nitrogen. Diethylaminosulphur trifluoride (30.32 g) in dry methylene chloride (5 ml) was added slowly, maintaining the temperature at −70° C. After completion of the addition, the mixture was stirred at −70° C. for 1 hour and was then allowed to warm to room temperature, stood for 3 hours and then overnight. The reaction was then carefully added to ice with vigorous stirring, and the resultant methylene chloride layer combined with a further methylene chloride extract of the aqueous layer. The total organic fraction was washed with brine, dried over magnesium sulphate and the solvent carefully distilled, to leave ethyl 2-fluoro-isobutyrate as a bronze liquid (12.8 g); $^1$H NMR analysis indicated that this material was >95% pure, and contained 2–3% of ethyl methacrylate. NMR (CDCl$_3$, 270 MHz) δ 1.31(3H,t), 1.58(6H,d), 4.25 (2H,q) ppm; $^1$H NMR (CDCl$_3$, 254 MHz, $^{19}$F) δ −148.0 (1F, septet) ppm.

EXAMPLE 2

This Example illustrates the preparation of ethyl 2-fluoroisobutyrate by Route 2.

Ethyl 2-hydroxyisobutyrate (19.8 g), anhydrous hydrogen fluoride (40 g) and sulphur tetrafluoride (20.2 g) were charged into a 100 ml monel autoclave and stirred for 40 minutes while warming to 0° C., from −36° C. The reaction was then heated to 30° C. and stirred for 14 hours. It was then cooled to room temperature and excess pressure vented to atmosphere through a sodium bicarbonate scrubber. The solution was then poured onto ice (150 g), water added (500 ml) and the solution extracted with methylene chloride (120 ml). The organic extract was dried over magnesium sulphate, a little sodium bicarbonate added, and the solvents removed at atmospheric pressure by distillation through a short vigreux column, to give an oil (24.5 g). Hexane (150 ml) was then added, and after standing for 1 hour, the solution was filtered through celite, and the solvent distilled, to leave substantially pure ethyl 2-fluoroisobutyrate (17.0 g).

EXAMPLE 3

This Example illustrates the preparation of ethyl 2-fluoroisobutyrate by Route 3.

Ethyl 2-fluoropropionate (9.0 g) was slowly added to a stirred solution of lithium diisopropylamide (prepared by addition of 41 ml of a 2.5 molar solution of n-butyl lithium in hexane, to 10.4 g of diisopropylamine at −20° C.) in dry THF (110 ml) at −70° C. under nitrogen. After completion of the addition the reaction was stirred for 1 hour at −70° C. Methyl iodide (31.95 g) in dry THF (10 ml) was then added slowly, dropwise. After completion of the addition the reaction mixture was warmed to room temperature and stirred overnight. Water was then carefully added at −5° C. and the mixture extracted thoroughly with diethyl ether. The ether solution was dried over magnesium sulphate and then the ether carefully distilled leaving a bronze liquid, which was then distilled to give a main fraction (5.35 g), which NMR analysis indicated contained 65% ethyl 2-fluoroisobutyrate and 35% ethyl 2-fluoropropionate.

EXAMPLE 4

This Example illustrates the preparation of 2-fluoroisobutyric acid by Route 4.

2-Fluoropropionic acid (1.84 g) in dry THF was added slowly over 0.5 hour to a stirred solution of lithium diisopropylamide (prepared by addition of 24 ml of a 2.5 molar solution of n-butyl lithium in hexane, to 6.06 g diisopropylamine at −20° C.) in dry THF (60 ml) at −70° C., under nitrogen. After completion of the addition the mixture was stirred for 1 hour, and methyl iodide (8.52 g) was added slowly over 40 minutes, keeping the temperature at −70° C. After a further 30 minutes the reaction was warmed to room temperature and then stirred for 24 hours. Water was then carefully added at 5° C. The organic layer was separated and the aqueous layer acidified with concentrated hydrochloric acid, and was then extracted with diethyl ether. The ether solution was washed with brine, dried over magnesium sulphate, and evaporated to give a bronze oil (1.27 g). NMR analysis showed that the oil was 80% 2-fluoroisobutyric acid, and 20% starting 2-fluoropropionic acid.

Similarly prepared were:
2-fluoro-2-methylbutanoic acid $^1$H NMR (270 MHz; CDCl$_3$) δ 1.01(3H,t), 1.60(3H,d), 2.00(2H,m) ppm.
2-ethyl-2-fluoro butanoic acid $^1$H NMR (270 MHz; CDCl$_3$) δ 0.99(6H,t), 1.89(4H,m) ppm.
2-fluoro-2,3-dimethylbutanoic acid $^1$H NMR (270 MHz; CDCl$_3$) δ 1.02(6H,dd), 1.65(3H,dd), 2.14(1H,m) ppm.
2-fluoro-2-methylpent-4-ynoic acid $^1$H NMR (270 MHz; CDCl$_3$) δ 1.70(3H,d), 2.15(1H,m), 2.84(2H,m) ppm.
2-fluoro-2-methylpent-4-enoic acid $^1$H NMR (270 MHz; CDCl$_3$) δ (inter alia) 1.62(3H,m), 2.46(2H,m), 5.8(1H,m) ppm.
2-fluoro-2-methylpentanoic acid $^1$H NMR (270 MHz; CDCl$_3$) δ 0.95(3H,t), 1.45(2H,m), 1.63(3H,d), 1.95(2H,m) ppm.

EXAMPLE 5

This Example illustrates the preparation of 2-fluoroisobutyric acid by Route 5.

Ethyl 2-fluoroisobutyrate (10.2 g) was heated with 50% sulphuric acid (100 ml) at 85° C. for 5 hours, stood overnight at room temperature and then heated at 85° C. for a further 4 hours. After cooling the mixture was poured into saturated brine and extracted well with methylene chloride. The organic extract was dried over magnesium sulphate, and carefully evaporated at below 35° C., to give 2-fluoroisobutyric acid. NMR analysis indicated that the material was 90% pure, containing about 5% of the starting ester and 5% of methacrylic acid; $^1$H NMR (CDCl$_3$, 270 MHz) δ 1.65 (6H,d) ppm; $^1$H NMR (CDCl$_3$, 254 MHz, $^{19}$F) δ −148.3 (1F, septet) ppm; IR (liquid film) ν: 3400–2700(b), 1735(s) cm$^{-1}$.

EXAMPLE 6

This Example illustrates the preparation of 2-fluoroisobutyric acid by Route 6.

Ethyl 2-fluoroisobutyrate (0.50 g), was stirred vigorously overnight at room temperature with 2M aqueous sodium hydroxide (10 ml) and methylene chloride (10 ml) containing cetrimide (0.050 g). The aqueous layer was washed with methylene chloride, acidified with dilute hydrochloric acid and extracted again with methylene chloride. The extracts were dried over magnesium sulphate and evaporated to give 2-fluoroisobutyric acid as an oil (0.200 g).

EXAMPLE 7

This Example illustrates the preparation of 2-fluoroisobutyric acid by Route 6.

Ethyl 2-fluoroisobutyrate (2.0 g) was stirred in ethanol (10 ml) containing dissolved sodium hydroxide (1.20 g), for 2 hours at room temperature. The ethanol was then evaporated and the residue treated with 2M aqueous hydrochloric acid, and extracted with methylene chloride. The organic extract was dried over magnesium sulphate and evaporated to give 2-fluoroisobutyric acid (1.45 g).

EXAMPLE 8

This Example illustrates the preparation of 2-fluoroisobutyryl chloride by Route 7.

Oxalyl chloride (0.679 g) in dry deuterochloroform (2 ml) was added dropwise to a stirred solution of 2-fluoroisobutyric acid (0.567 g) in dry deuterochloroform (3 ml), at room temperature. Halfway through the addition one drop of DMF was added. After stirring for 2 hours the solution contained 2-fluoroisobutyryl chloride, which could be used without further purification; $^1$H NMR (CDCl$_3$, 270 MHz) δ 1.68 (6H,d) ppm; $^1$H NMR (CDCl$_3$, 254 MHz, $^{19}$F) δ —137.7 (1F, multiplet) ppm; IR (CDCl$_3$) v: 1800, 1780 cm$^{-1}$.

EXAMPLE 9

This Example illustrates the preparation of 2-fluoro-2-fluoromethylpropanoic acid by Route 8.

Step 1

Preparation of 1-benzoyloxy-2-methyl-3-fluoropropan-2-ol (and isomer)

A mixture of 1-benzoyloxymethyl-1-methyloxirane (9.6 g) and triethylamine/HF complex (16 g) were heated together at 90° C. for 2 hours and subsequently kept at room temperture overnight. Further heating at 90° C. for 8 hours was followed by keeping at room temperature overnight. The mixture was carefully added to saturated aqueous sodium hydrogen carbonate and repeatedly extracted with ether. The combined organic extracts were washed with water, dried (MgSO$_4$) and concentrated under reduced pressure to give a pale yellow viscous oil (8.2 g). This product was shown by NMR to be a 2.5:1 mixture of 1-benzoyloxy-2-methyl-3-fluoropropan-2-ol (1) and 3-benzoyloxymethyl-2-fluoro-2-methylpropan-1-ol (2) respectively and was used in the next step without further purification.

(1):$^1$H NMR (270 MHz, CDCl$_3$) δ 1.33 (3H,d), 2.60(1H,s), 4.36(2H,s), 4.49(2H,d), 7.47(2H,t), 7.59(1H,t), 8.05(2H,d); (2):$^1$H NMR (270 MHz, CDCl$_3$) δ 1.48 (3H,d), 2.5(1H,bs), 3.74(2H,bd), 4.39–4.58(2H,m), 7.45 (2H,t), 7.58(1H,t), 8.05(2H,d) ppm.

Step 2

Preparation of 1-benzoyloxymethyl-1,2-difluoropropane

The product from step 1 (8.2 g) was dissolved in dry dichloromethane (50 ml) and the solution stirred under a nitrogen atmosphere at 0° C. Diethylaminosulphur trifluoride (6.2 ml) was added portionwise over 15 minutes and, after a further 30 minutes, the reaction was allowed to warm to room temperature and left to stand overnight. The mixture was poured into water (500 ml) and extracted with hexane (2×150 ml). The combined extracts were washed with saturated aqueous sodium bicabonate, dried (MgSO$_4$) and concentrated under reduced pressure to give the product as a mobile yellow oil (5.3 g; 64%); $^1$H NMR (270 MHz, CDCl$_3$) δ 1.51 (3H,dd), 4.39–4.67(4H,m), 7.48(2H,t), 7.60 (1H,t), 8.06(2H,d); $^{19}$F $^1$H NMR (270 MHz, CDCl$_3$) δ 232.3(1F,dt), 163.6(1F,m) ppm.

Step 3

Preparation of 2-fluoro-2-fluoromethylpropan-1-ol

The product from step 2 (7.8 g) was stirred at room temperature in a solution of NaOH in methanol (15 ml; 1%). After 1 hour (when gc analysis showed the absence of starting material), the mixture was neutralised with the calculated amount of acetic acid (215 µl). The methanol was removed by distillation, and the residue distilled at 50 mmHg. The fraction boiling between 80°–85° C. was iso-lated and shown by NMR to consist of the title compound containing approximately 20 mole percent of methyl benzoate. $^1$H NMR (270 MHz, CDCl$_3$) δ 1.39(3H,dd), 2.00(1H, bs), 3.69(1H,d), 3.76(1H,d), 4.45(1H,d), 4.51(1H,d) ppm.

Step 4

Preparation of 2-fluoro-2-fluoromethylpropanoic Acid

The product from step 3 (1.13 g) was dissolved in acetone (45 ml) and the solution stirred with ice bath cooling. A solution of Jones reagent was added [prepared from chromium trioxide (5.0 g), concentrated sulphuric acid (2.5 ml) and water (22.5 ml)], the cooling bath was removed and the mixture was allowed to warm to room temperature. After 28 hours, sufficient water was added to redissolve the precipitated chromium salts and the mixture was repeatedly extracted with dichloromethane. The combined organic extracts were dried (MgSO$_4$) and concentrated under reduced pressure to give the title acid as a pale yellow oil (800 mg); $^1$H NMR (270 MHz, CDCl$_3$) δ 1.62(3H,dd), 4.38–4.90(2H,m), 8.3(1H,bs) ppm.

EXAMPLE 10

This Example illustrates the preparation of 2-fluoro-2-methylbutyric acid by Route 4.

2-Fluoropropionic acid (2.0 g) was slowly added (as a solution in dry THF, 5 ml) to lithium diisopropylamide (freshly made from 26 ml of n-butyl lithium and 6.59 g of dry diisopropylamine) in dry THF (40 ml) at –70° C. under nitrogen. After completion of the addition the orange solution was stirred for 30 minutes, and ethyl iodide (10.17 g) in dry THF (15 ml) was added slowly dropwise. The reaction was then allowed to warm up slowly to room temperature overnight. It was then worked up by cooling and treating carefully with dilute hydrochloric acid, followed by extraction with ether. The ethereal solution was dried over magnesium sulphate, and evaporated to give the title acid as a bronze coloured oil, (0.89 g); $^1$H NMR (270 MHz, CDCl$_3$) δ 1.05(3H,t), 1.60(3H,d), 1.80–2.10(2H,m), 6.90 (1H,vbs) ppm.

EXAMPLE 11

This Example illustrates the preparation of 2-fluoro-2-methylpentanoic acid by Route 4.

Using the procedure of Example 10, except using n-propyl iodide in place of ethyl iodide, the title compound was obtained; $^1$H NMR (270 MHz, CDCl$_3$) δ 0.95(3H,t), 1.20–1.60(2H,m), 1.62(3H,d), 1.70–2.05(2H,m), 6.70(vbs) ppm.

EXAMPLE 12

This Example illustrates the preparation of methyl 2-fluoromethyl-2,3,3,3-tetrafluoropropanoate by Route 9.

Step 1

Preparation of methyl 2-hydroxymethyl-2,3,3,3-tetrafluoropropanoate

Methyl 2,3,3,3-tetrafluoropropanoate (27.0 g) was dissolved in dry dichloromethane and the solution stirred under a dry nitrogen atmosphere at 0° C. A one molar solution of di-n-butylboron trifluoromethanesulfonate in dichloromethane (190 ml) was added in portions over 15 minutes. After a further 15 minutes, the temperature was reduced to −10° C. and di-isopropylethylamine (35 ml) was added in portions, then stirring was continued for a further 2 hours. Paraformaldehyde (100 g) (previously dried under vacuum over $P_2O_5$) was heated to 180°–200° C. and the resulting formaldehyde was passed into the reaction mixture in a stream of dry nitrogen, keeping the temperature close to −10° C. After 30 minutes, the mixture was poured into a mixture of 30% aqueous hydrogen peroxide (150 ml) pH7 phosphate buffer (600 ml) and crushed ice, and was stirred at 0° C. for 45 minutes. The mixture was extracted with dichloromethane (3×200 ml). The combined extracts were washed with sodium disulphite solution, dried ($MgSO_4$) and concentrated under reduced pressure to leave a yellow oil, which was redissolved in ethyl acetate and filtered through a thick plug of silica gel, and then was again concentrated under reduced pressure. The crude product was purified by chromatography on silica, eluting with 25% ethyl acetate in hexane. Subsequent heating to 65° C. under aspirator vacuum (20 mmHg) gave the product as a yellow oil (4.8 g); $^1$H NMR (270 MHz; $CDCl_3$) δ 3.93(3H,s), 4.05–4.30(2H, m), 2.80(1H,bt) ppm.

Step 2

Preparation of Methyl 2-fluoromethyl-2,3,3,3-tetrafluoropropanoate

The product from step 1 (600 mg) was dissolved in dry dichloromethane (5 ml) and was stirred under an atmosphere of dry nitrogen at 0° C. Diethylamino-sulphurtrifluoride (DAST) (420 µl) was added in portions, stirring was continued 30 minutes at 0° C. and the mixture was left at room temperature overnight. A further portion of DAST (200 µl) was added and the mixture left for 24 hours. Water was added, the mixture was stirred, then the organic phase was separated and washed with saturated aqueous sodium hydrogen carbonate (5 ml) and was dried ($MgSO_4$). After concentration at atmospheric pressure, the product was distilled in a kugelrohr oven (50° C., 100 mmHg), giving the product as a colourless oil (320 mg); $^1$H NMR (270 MHz; $CDCl_3$) δ 3.97(3H,s), 4.70–5.12(2H,m) ppm.

EXAMPLE 13

This Example illustrates the preparation of methyl 2-fluoro-2-trifluoromethylbut-3-enoate by Route 9.

Step 1

Preparation of Methyl 2-fluoro-2-trifluoromethyl-3-hydroxybutanoate

Dibutylboron triflate (5 g) was added to a stirred solution of methyl 2,3,3,3-tetrafluoropropionate (2.9 g) in dichloromethane at 0° C. under nitrogen. After 15 minutes, the solution was cooled to −10° C. and diisopropylethylamine (3.8 ml) was added in portions. After 30 minutes, freshly distilled acetaldehyde (2 ml) was added in small portions, keeping the temperature at −10° C. The reaction was stirred at −10° C. for 1 hour before quenching with a mixture of pH7 phosphate buffer (60 ml), aqueous hydrogen peroxide (100 vol; 15 ml) and crushed ice and stirring for 1.5 hours. The organic phase was separated and the aqueous layer further extracted with dichloromethane. The combined organic phases were washed with aquesous sodium metabisulphite and with brine, dried ($MgSO_4$) and concentrated under reduced pressure to give a pink oil (2.2 g) which was distilled using a Kugelrohr apparatus. The fraction distilling at 40° C. (air bath temperature) and at 0.05 mmHg was collected; $^1$H NMR (270 MHz; $CDCl_3$) (signals recorded for a 50:50 mixture of diastereomers) δ 1.34 (1.5H,d), 1.42 (1.5H,d), 2.2(1H,bs), 3.91(1.5H,bs), 3.94(1.5H,s), 4.35–4.52(1H,m) ppm.

Step 2

Preparation of Methyl 2-fluoro-2-trifluoromethylbut-3-enoate

Methyl 2-fluoro-2-trifluoromethyl-3-hydroxybutanoate (1 g) and pyridine (440 µl) in dichloromethane (5 ml) were stirred at −10° C. under nitrogen. Trifluoromethanesulphonic anhydride (900 µl) in dichloromethane (5 ml) was added dropwise and the resulting mixture stirred for 2 hours. The solution of methyl 2-fluoro-2-trifluoromethyl-3-trifluoromethylsulphonyloxybutanoate prepared in Step 1 was treated with 1,8-diazabicyclo[5.4.0]undec-7-ene (DBU) (1.5 ml) and heated under reflux for 1 hour. Further DBU (1.5 ml) was added and the mixture left to stand at room temperature overnight. The red solution was washed with 5% aqueous HCl, saturated aqueous sodium bicarbonate (twice), dried ($MgSO_4$) and concentrated at atmospheric pressure to give a red oil which was distilled using a Kugelrohr apparatus. The fraction distilling at 50° C. (air bath temperature) and at 100 mmHg was shown by NMR to be the desired product; $^1$H NMR (270 MHz; $CDCl_3$) δ 3.92 (3H,s), 5.65(1H,dd), 5.81(1H,d), 6.08(1H,ddd) ppm.

CHEMICAL FORMULAE
(in description)

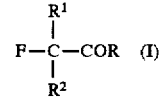

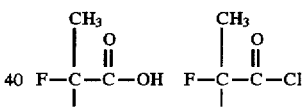

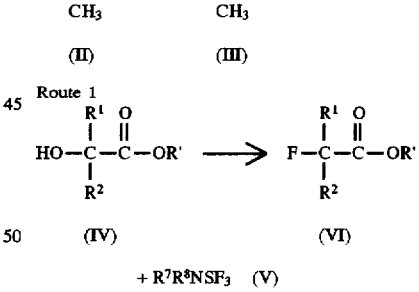

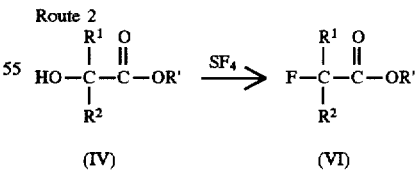

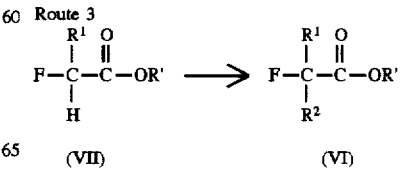

-continued
CHEMICAL FORMULAE
(in description)

Route 4
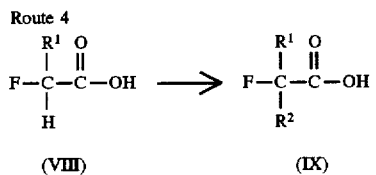

Route 5
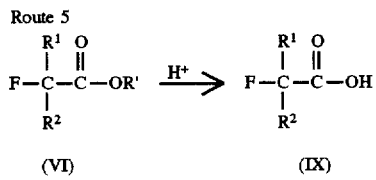

Route 6
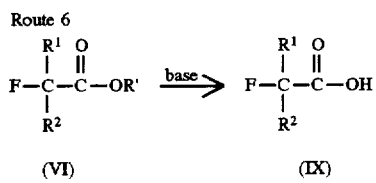

Route 7
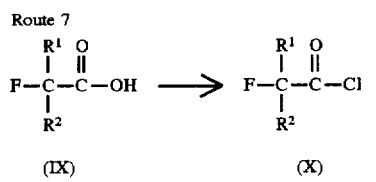

Route 8
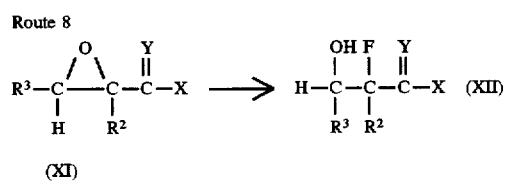

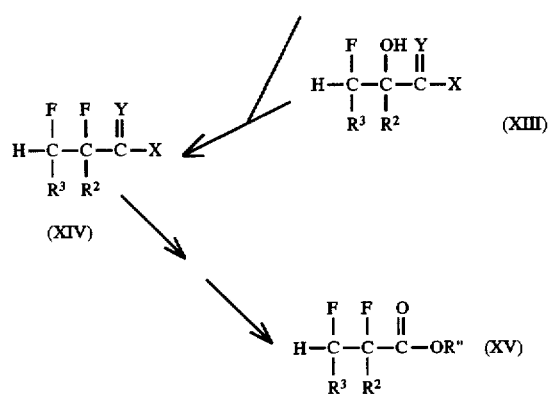

-continued
CHEMICAL FORMULAE
(in description)

Route 9
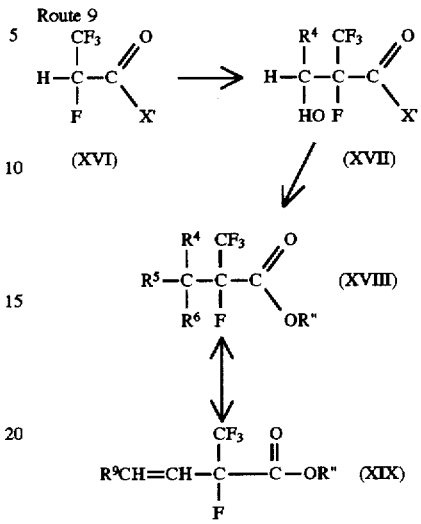

I claim:

1. A compound of the formula (I):

wherein R is OH, Cl, $C_{1-8}$ alkoxy or optionally substituted benzyloxy; $R^1$ is methyl, ethyl, $CH_2F$ or $CF_3$; and, when $R^1$ is methyl, ethyl or $CH_2F$, $R^2$ is ethyl, n- or iso-propyl, optionally substituted benzyl or $CHFR^3$ wherein $R^3$ is H, methyl or ethyl, and, when $R^1$ is $CF_3$, $R^2$ is the group $C(R^4)(R^5)R^6$ wherein $R^4$ is H, methyl or ethyl, $R^5$ is H, F, Br, methyl or ethyl and $R^6$ is H or F, or $R^1$ and $R^2$ are both methyl and R is Cl, $C_{3-8}$ alkoxy or OH, the compounds in which R is OH or Cl having a purity of 80% or more; provided that when $R^1$ is methyl and $R^2$ is ethyl or benzyl, R is not methoxy or ethoxy, that when $R^1$ is methyl and $R^2$ is $CH_2F$, R is not methoxy, that when $R^1$ and $R^2$ are both ethyl, R is not OH, methoxy or ethoxy and that when $R^1$ is $CF_3$ and $R^2$ is methyl, R is not methoxy.

2. 2-Fluoroisobutyric acid having a purity of 80% or more.

3. 2-Fluoroisobutyric acid as claimed in claim 4 in the absence of isobutyric acid or 3-fluoroisobutyric acid.

4. 2-Fluoroisobutyric acid having a purity of at least 90%.

5. 2-Fluoroisobutyryl chloride having a purity of 80% or more.

6. 2-Fluoroisobutyryl chloride in the absence of isobutyryl chloride.

7. 2-Fluoroisobutyryl chloride in the absence of 3-fluoroisobutyryl chloride.

* * * * *